United States Patent [19]

Gregory et al.

[11] 4,371,516

[45] Feb. 1, 1983

[54] ARTICLES FOR CARRYING CHEMICALS

[75] Inventors: George K. E. Gregory, Marlow; James M. Peach, High Wycombe; James D. Du Mayne, Maidenhead, all of England

[73] Assignee: John Wyeth & Brother Limited, Maidenhead, England

[21] Appl. No.: 284,025

[22] Filed: Jul. 17, 1981

Related U.S. Application Data

[63] Continuation of Ser. No. 837,345, Sep. 28, 1977, abandoned.

[30] Foreign Application Priority Data

Oct. 6, 1976 [GB] United Kingdom ............... 41483/77

[51] Int. Cl.$^3$ .............................................. A61K 9/26
[52] U.S. Cl. .................................................. 424/22
[58] Field of Search ........................................ 424/22

[56] References Cited

U.S. PATENT DOCUMENTS

| | | | |
|---|---|---|---|
| 2,166,074 | 7/1939 | Reichel | 424/22 |
| 3,234,091 | 2/1966 | Lang et al. | 424/22 |
| 3,576,760 | 4/1971 | Gould et al. | 424/22 |
| 3,855,712 | 12/1974 | Blonde | 424/22 |

FOREIGN PATENT DOCUMENTS

| | | | |
|---|---|---|---|
| 840409 | 4/1970 | Canada | 424/22 |
| 2017373 | 4/1970 | Fed. Rep. of Germany | 424/22 |
| 2335205 | 9/1973 | France | 424/22 |
| 2199973 | 4/1974 | France | 424/22 |
| 466235 | 6/1936 | United Kingdom | 424/22 |
| 590725 | 10/1942 | United Kingdom | 424/22 |
| 849830 | 9/1960 | United Kingdom | 424/22 |
| 860877 | 2/1961 | United Kingdom | 424/22 |
| 903506 | 8/1962 | United Kingdom | 424/22 |
| 907181 | 10/1962 | United Kingdom | 424/22 |
| 1310824 | 3/1973 | United Kingdom | 422/22 |

*Primary Examiner*—Henry R. Jiles
*Assistant Examiner*—Robert C. Whittenbaugh
*Attorney, Agent, or Firm*—Arthur E. Wilfond

[57] ABSTRACT

The invention relates to shaped articles carrying chemicals, particular to pharmaceutical dosage forms carrying pharmaceuticals, which disintegrate rapidly in water. The shaped articles comprise an open matrix network of carrier material carrying the chemical. The articles may be prepared by subliming solvent from a composition comprising the chemical and a solution of the carrier material in a solvent, the composition being in the solid state in a mould.

5 Claims, No Drawings

ARTICLES FOR CARRYING CHEMICALS

This is a continuation, of application Ser. No. 837,345, filed Sept. 28, 1977 now abandoned.

This invention relates to articles for carrying chemicals, to a method of preparing such articles, and to packages containing the articles.

Many pharmaceuticals are administered orally in the form of solid shaped articles such as tablets, pills and capsules. Generally the tablet, pill or capsule has to be swallowed from the mouth to the stomach to enable the pharmaceutical to be absorbed in the gastro-enteric system. However, in some cases there is the problem that swallowing is difficult or not feasible. Some subjects, particularly paediatric and geriatric patients, may be unco-operative and spit the tablet out instead of swallowing it. A similar difficulty can be present in administering pharmaceuticals to non-human animals in veterinary treatment in that animals may also be unco-operative about taking tablets. The invention, in one aspect, seeks to avoid this problem by providing a pharmaceutical dosage form that disintegrates rapidly in the mouth. Some embodiments of the invention dissolve so rapidly in the saliva of the mouth, for instance, in one or two seconds, that there is hardly time for an unco-operative subject to spit the product out. Although the remarks given above concern oral preparations the pharmaceutical dosage forms of the invention have a wider application in that they may be administered to other body cavities or to wounds where they will be broken down, with rapid release of the pharmaceutical, by aqueous media other than saliva.

In addition, it is often desired to add a predetermined amount of chemical (not necessarily a pharmaceutical) to an aqueous medium. For example, the chemical may be a diagnostic compound which it is desired to add to a biological sample, such as a sample of urine or blood, for determining the amount of a particular constituent present in the sample. Alternatively, it may be desired to add a predetermined amount of chemical reagent to a known amount of aqueous liquid to produce a standardised liquid which can be used, for example, in chemical analysis. Again the chemical may be a water soluble or water dispersible pharmaceutical which can be added to a known amount of aqueous medium to form a pharmaceutical solution or dispersion which can be used in the usual way for administering the pharmaceutical such as by injection or inhalation. Further, certain chemicals are difficult or hazardous to handle in solution or suspension and it may be desirable to convert them into a solid form which can be subsequently added to an aqueous medium to produce a solution or dispersion of the chemical. In all these instances it is desirable that when the chemical is added to the aqueous medium the chemical should dissolve rapidly or be dispersed uniformly throughout the medium.

Accordingly the present invention provides a shaped article carrying a chemical, the article being capable of being rapidly disintegrated by water and comprising an open matrix network carrying the chemical, the open matric network being comprised of a water-soluble or water-dispersible carrier material that is inert towards the chemical.

Preferably the shaped article is a pharmaceutical dosage form carrying a pharmaceutical substance. Thus, according to a preferred feature, the invention provides a pharmaceutical dosage form which can be rapidly disintegrated by water and which comprises an open matrix network carrying a pharmaceutical substance, the open matrix network being comprised of a pharmacologically acceptable water-soluble or water-dispersible carrier material.

By "rapidly disintegrated" is meant that the shaped articles are disintegrated in water within 10 seconds. Preferably the shaped article disintegrates (dissolves or disperses) within 5 seconds or less. The disintegration time is measured by a procedure analogous to the Disintegration Test for Tablets, B.P. 1973. The procedure is described below:

Apparatus

A glass or suitable plastic tube 80 to 100 mm long, with an internal diameter of about 28 mm and an external diameter of 30 to 31 mm, and fitted at the lower end, so as to form a basket, with a disc of rustproof wire gauze complying with the requirements for a No. 1.70 sieve.

A glass cylinder with a flat base and an internal diameter of about 45 mm containing water not less than 15 cm deep at a temperature between 36° and 38° C.

The basket is suspended centrally in the cylinder in such a way that it can be raised and lowered repeatedly in a uniform manner so that at the highest position the gauze just breaks the surface of the water and at the lowest position the upper rim of the basket just remians clear of the water.

Method

Place one shaped article in the basket and raise and lower it in such a manner that the complete up and down movement is repeated at a rate equivalent to thirty times a minute. The shaped articles are disintegrated when no particle remains above the gauze which would not readily pass through it. No such particle should remain after 10 seconds.

By the term "open matrix network" there is meant a network of water-soluble or water-dispersible carrier material having interstices dispersed throughout. The open matrix network of carrier material is of generally low density. For example the density may be within the range 10 to 200 mg/cc e.g. 10 to 100 mg/cc, preferably 30 to 60 mg/cc. The density of the shaped article may be effected by the amount of pharmaceutical substance or other chemical, or any other ingredients, incorporated into the article and may be outside the above mentioned preferred limits for the density of the matrix network. The open matrix network which is similar in structure to a solid foam enables a liquid to enter the product through the interstices and permeate through the interior. Permeation by aqueous media exposes the carrier material of both the interior and exterior of the product to the action of the aqueous media whereby the network of carrier material is rapidly disintegrated. The open matrix structure is of a porous nature and enhances disintegraton of the product as compared with ordinary solid shaped pharmaceutical dosage forms such as tablets, pills, capsules, suppositories and pessaires. Rapid disintegration results in rapid release of any pharmaceutical substantial or other chemical carried by the matrix.

The carrier material used in the product of the invention may be any water-soluble or water-dispersible material that is pharmacologically acceptable or inert to the chemical and which is capable of forming a rapidly disintegratable open matrix network. We prefer to use water-soluble material as the carrier since this results in the most rapid disintegration of the matrix when the product is placed in an aqueous medium. We have found that a particularly advantageous carrier may be formed from polypeptides such as gelatin, particularly gelatin which is particularly hydrolysed, e.g. by heating in water. For example, the gelatin may be partially hydrolysed by heating a solution of the gelatin in water, e.g. in an autoclave at about 120° C. for up to 2 hours, e.g. from about 5 minutes to about 1 hour, preferably from about 30 minutes to about 1 hour. The hydrolysed gelatin is preferably used at concentrations of about 1 to 6% weight/vol., most preferably at 2 to 4% e.g. about 3%. Other carrier materials may be used in place of partially hydrolysed gelatin for example polysaccharides such as hydrolysed dextran, dextrin and alginates (e.g. sodium alginate) or mixtures of above mentioned carriers with each other or with other carrier materials such as polyvinyl alcohol, polyvinylpyrrolidine or acacia.

The pharmaceutical dosage form of the invention may be employed to administer a wide variety of pharmaceutical substances. In this specification the term "pharmaceutical substances" not only includes medicaments for administration to human and non-human animals but also contraceptives (particularly oral contraceptives). Typical drugs which can be administered by means of this invention include, for example, drugs for treating coronary disorders, e.g. digoxin; oral vaccines; enzymes; anti-anginal drugs, e.g. glyceryl trinitrate; peripheral vasodilators and anti-hypertensives e.g. indoramin; vasoconstrictors, e.g. ergotamine; analgesics e.g. meptazinol, pentazocine; hypnotics; major and minor tranquillizers e.g. lorazepam, oxazepam, temazepam; anti-depressants e.g. ciclazindol; anti-convulsants e.g. clonazepam; CNS stimulants e.g. pemoline; muscle relaxants e.g. orphenadrine; neuro-muscular drugs e.g. pyridostigmine; gonadal hormones and oral contraceptives e.g. ethynyl oestradiol, norgestrel; corticosteroids e.g. prednisolone; local anaesthetics; anti-inflammatories e.g. oxaprozin; drugs acting on the uterus e.g. hyoscine butyl bromide; spermicides e.g. nonoxynol-9; anti-allergics e.g. triprolidine and drugs relieving poisoning and metabolic dysfunction e.g. methysergide. The pharmaceutical dosage form is particularly useful for oral administration of drugs. This form of administration can be used for administration of drugs which are normally absorbed via the gastro intestinal tract but is also useful for administration of drugs (e.g. nitroglycerin) via the buccal route since such drugs may be very rapidly absorbed by the use of the present invention.

The shaped articles of the present invention may incorporate ingredients in addition to the chemical or pharmaceutical substance. For example the pharmaceutical dosage form of the present invention may incorporate pharmaceutically acceptable adjuvants. Such adjuvants include, for example, colouring agents, flavouring agents, preservations (e.g. bacteriostatic agents), and the like.

The shaped articles of the present invention may be prepared by a process which comprises subliming solvent from a composition comprising the chemical (e.g. pharmaceutical substance) and a solution of the carrier material in a solvent, the composition being in the solid state in a mould.

The sublimation is preferably carried out by freeze drying a composition comprising the chemical (e.g. pharmaceutical substance) and a solution of the carrier material in a solvent. The composition may include additional ingredients, such as those mentioned above. The solvent is preferably water but it may contain a co-solvent (such as an alcohol e.g. tert-butyl alcohol) to improve the solubility of the chemical. The composition may also contain a surfactant e.g. Tween 80 [polyoxyethylene (20) sorbitan mono-oleate]. The surfactant may help to prevent the freeze dried product sticking to the surface of the mould. It may also aid in the dispersion of the chemical.

The mould may comprise a series of cylindrical or other shape depressions in it, each of a size corresponding to the desired size of the shaped article. Alternatively, the size of the depression in the mould may be larger than the desired size of the article and after the contents have been freeze dried the product can be cut into the desired size (for example thin wafers).

In one embodiment the mould comprises a metal plate (e.g. an aluminum plate) containing one or more depressions. In a preferred process using such a mould, the mould is cooled with a cooling medium (e.g. liquid nitrogen or solid carbon dioxide). When the mould is cooled a predetermined amount of water containing the carrier material, the chemical (e.g. pharmaceutical substance) and any other desired ingredient is fed into the depression(s). When the contents of the depression(s) are frozen the mould is subjected to reduced pressure and, if desired, controlled application of heat to aid the sublimation. The pressure can be below about 4 mm. Hg; we prefer to employ pressures of below 0.3 mm Hg, for example 0.1 to 0.2 mm. The freeze dried products may then be removed from the depressions in the mould and stored for future use, e.g. in airtight jars or other suitable storage containers.

The following Examples illustrate the invention.

EXAMPLE 1

(a) Preparation of hydrolysed gelatin solution
  Gelatin B.P.—30.00 g.
  Purified water to—1000.00 ml.

The gelatin is dissolved in the water with the aid of heat and constant stirring. The resulting solution is autoclaved at 121° C. (15 p.s.i.) for one hour. The solution is allowed to cool to room temperature.

(b) Preparation of pharmaceutical dosage form
  Lorazepam—1.00 g.
  Colour (F.D.C. Yellow No. 5)—0.25 g.
  Orange flavour (Norda spray dried)—0.5 g.
  Gelatin solution to—1000.00 ml.

An aluminium mould containing 75 cylindrical depressions (each depression being about 0.5 cm diameter and 1 cm deep) is cooled to about −192° C. in liquid nitrogen contained in a stainless steel tray. The lorazepam, colour and flavour are mixed with the gelatin solution and mixing continued while ¼ ml. of the mixture is injected by hypodermic syringe into each depression. When the contents of each depression are frozen the mould is placed into a vacuum chamber at room temperature and a vacuum of 0.3 mm Hg. is supplied overnight. The freeze dried pharmaceutical dosage forms, each containing 0.5 mg. of lorazepam, are then removed from the depressions and stored in airtight jars.

The pharmaceutical dosage forms disintegrate rapidly, for example, in two seconds or less, when taken orally.

EXAMPLE 2

The method of Example 1(b) is repeated substituting 2.00 g. nitroglycerin for the 1.00 g. lorazepam and using appropriate pharmaceutically acceptable colours and flavours to give pharmaceutical dosage forms each containing 1.00 mg. of nitroglycerin.

EXAMPLE 3

The method of Example 1(b) is repeated substituting 2.00 g. digoxin for the 1.00 g. lorazepam and using appropriate pharmaceutically acceptable colours and flavours to give pharmaceutical dosage forms each containing 1.00 mg. of digoxin.

EXAMPLE 4

The method of Example 1(b) is repeated substituting 2.00 g. ergotamine for the 1.00 g. lorazepam and using appropriate pharmaceutically acceptable colours and flavours to give pharmaceutical dosage forms each containing 1.00 mg. of ergotamine.

EXAMPLES 5-11

The method of Example 1(b) is repeated substituting the following compositions for that given in Example 1(b).

EXAMPLE 5

Lorazepam—5 g.
Tween 80 [polyoxyethylene (20) sorbiton monoleate-]—0.5 g.
Sucrose—30 g.
Gelatin solution [from Example 1(a)]—to 1000 ml.
0.5 ml of the above composition is added to each depression

EXAMPLE 6

Meptazinol—80 g.
Sucrose—40 g.
Gelatin solution [from Example 1(a)]—to 1000 ml.
0.5 ml of the above composition is added to each depression

EXAMPLE 7

Oxaprozin—200 g.
Sucrose—40 g.
Gelatin solution [from Example 1(a)]—to 1000 ml.
0.5 ml of the above composition is added to each depression, the oxaprozin being dispersed in the gelatine solution with the aid of ultrasonic vibrations.

EXAMPLE 8

Lorazepam—3.33 g.
Sodium alginate—17 g.
Dextran (m. wt. approx 40,000)—35 g.
Dextrose—17.5 g.
Distilled water—to 1000 ml.
0.75 ml of a suspension of the above composition is added to each depression, the lorazepam being suspended in the water containing sodium alginate, dextran and dextrose with the aid of ultrasonic vibrations.

EXAMPLE 9

Lorazepam—3.33 g.
Dextrin—50 g.
Polyvinylpyrrolidine—30 g.
Tween 80—0.2 g.
Distilled water to—1000 ml.
0.75 ml of the above composition is added to each depression.

EXAMPLE 10

Lorazepam—3.33 g.
Polyvinylalcohol (m. wt. approx 1400)—20 g.
Polyvinylpyrrolidine—20 g.
Sucrose—30 g.
Tween 80—0.2 g.
Distilled water—to 1000 ml.

The polyvinylalcohol is dissolved in about 50 ml of hot distilled water and the solution cooled. The polyvinylpyrrolidine, sucrose and Tween 80 are added and the mixture shaken until all the solids are dissolved. The lorazepam is added and dispersed with the aid of ultrasonic vibrations. The final volume of solution is adjusted to 1000 ml. with distilled water and 0.75 ml. of the solution added to each depression.

EXAMPLE 11

Lorazepam—3.33 g.
Acacia—20 g.
Sucrose—30 g.
Polyvinylpyrrolidine—30 g.
Tween 80—0.2 g.
Distilled water to—1000 ml.

The acacia is placed in a dry 1000 ml. volumetric flask. About 10 ml. of absolute alcohol is added and the flask shaken to wet the acacia powder. 500 ml. of distilled water is introduced and shaken to yield a homogeneous solution. The sucrose, polyvinylpyrrolidine, Tween 80 and lorazepam are dispersed into the solution with the aid of ultrasonic vibrations. The final volume is adjusted to 1000 ml. with distilled water and 0.75 ml. of the composition is added to each depression.

We claim:

1. A pharmaceutical dosage form for oral administration as a solid, which dosage form can be disintegrated by water within ten seconds and which consists essentially of an open matrix network carrying a unit dosage of a pharmaceutical substance, the open matrix network consisting essentially of a pharmacologically acceptable water-soluble or water-dispersible carrier material, selected from the group consisting of partially hydrolysed gelatin, hydrolysed dextran, alginate, and a mixture of at least one of the above carrier materials with polyvinyl alcohol, polyvinylpyrrolidine or acacia.

2. A process for preparing a pharmaceutical dosage form for oral administration as a solid which dosage form can be disintegrated by water within ten seconds, which process comprises subliming solvent from a composition consisting essentially of a pharmaceutical substance and a solution in a solvent of a pharmacologically acceptable water-soluble or water-dispersible carrier material selected from the group consisting of partially hydrolysed gelatin, hydrolysed dextran, alginate, and a mixture of at least one of the above carrier materials with polyvinyl alcohol, polyvinylpyrrolidine or acacia, the composition being in the solid state in a mold, corresponding in size and shape to that of the pharmaceutical dosage form, so as to produce an open matrix network of carrier material carrying the pharmaceutical substance, which matrix net-work is capable of being disintegrated by water within ten seconds.

3. The process of claim 2, wherein the composition contains a coloring agent, a flavoring agent or a preservative.

4. The process of claim 2, in which the solvent is water.

5. A method of orally administering a solid pharmaceutical dosage form to a mammal in need thereof, which comprises inserting into the mouth of said mammal a solid dosage form which can be disintegrated by water within ten seconds and which consists essentially of an open matrix network consisting essentially of a pharmacologically acceptable water-soluble or water-dispersible carrier material, selected from the group consisting of partially hydrolysed gelatin, hydrolysed dextran, alginate, and a mixture of at least one of the above carrier materials with polyvinyl alcohol, polyvinylpyrrolidine or acacia.

* * * * *